(12) United States Patent
Nagy et al.

(10) Patent No.: US 7,163,820 B1
(45) Date of Patent: Jan. 16, 2007

(54) *ESCHERICHIA COLI* STRAIN FOR AN ORAL VACCINE AGAINST POST-WEANING DIARRHEA IN PIGS

(75) Inventors: Bela Nagy, Budapest (HU); Ferenc Olasz, Budapest (HU); Zsolt Fekete, Budapest (HU)

(73) Assignee: MTA Allatorvos-Tudomanyi K.I., Budapest (HU)

( * ) Notice: Subject to any disclaimer, the term of this patent is extended or adjusted under 35 U.S.C. 154(b) by 0 days.

(21) Appl. No.: 09/958,081

(22) PCT Filed: Mar. 29, 2000

(86) PCT No.: PCT/HU00/00026

§ 371 (c)(1),
(2), (4) Date: Oct. 1, 2001

(87) PCT Pub. No.: WO00/58476

PCT Pub. Date: Oct. 5, 2000

(30) Foreign Application Priority Data

Mar. 31, 1999 (HU) .................... 9900836

(51) Int. Cl.
*C12N 1/00* (2006.01)
*C12N 15/00* (2006.01)
*C12N 1/20* (2006.01)
*C12N 15/63* (2006.01)
*C12N 15/09* (2006.01)
*A01N 63/00* (2006.01)
*A61K 48/00* (2006.01)

(52) U.S. Cl. ........................ 435/252.33; 435/252.1; 435/252.8; 435/320.1; 435/440; 435/848; 435/849; 435/243; 435/471; 424/93.1; 424/93.2; 424/93.4

(58) Field of Classification Search ............. 435/252.1, 435/235.1, 252.33, 252.8, 320.1, 440, 848, 435/849
See application file for complete search history.

(56) References Cited

U.S. PATENT DOCUMENTS

| 5,798,260 | A * | 8/1998 | Tarr et al. ................. 435/252.3 |
| 6,040,421 | A * | 3/2000 | Tarr et al. ................... 530/300 |
| 6,355,859 | B1 * | 3/2002 | Bosworth et al. .............. 800/8 |
| 6,596,923 | B1 * | 7/2003 | Bosworth et al. .............. 800/8 |
| 2004/0087522 | A1 * | 5/2004 | Marquardt et al. ............ 514/44 |

OTHER PUBLICATIONS

Nagy et al, Acta Vet. Hungarica, 1996, 44/1:9-19.*
Alexa et al, Vet. Med-Czech, 1995, 40/12:365-370.*
Moon et al, Vaccine, 1993, 11/2:213-220.*
Smith, CIBA Foundation Symposium, 1976, 42:45-72.*
Bosworth et al, Clinical and Diagnostic Laboratory Immunology, May 1998, 5/3:299-302.*
Bertschinger et al, Vet. Microbiol., 2000, 71:255-267.*
Rippinger et al, Vet. Microbiol., 1995, 45:281-295.*
da Silva et al, Vet. Microbiol., 2001, 80:227-233.*
Martins et al, Vet. Microbiol., 2000, 76:51-59.*
Sarrazin et al, Vet. Microbiol., 1997, 54:133-144.*
Amorim et al, Vet. Microbiol., 2000, 76:41-49.*
Frydendahl et al, Vet. Microbiol., 2003, 93:39-51.*
Krsnik et al, Comparative Immunology, Microbiology and Infectious Diseases, 1999, 22:261-273.*
Dean-Nystrom et al, J. Vet. Diagn. Invest., 1997, 9:77-79.*
Kwon et al, Vet. Record, 2002, 150:35-37.*
Sarrazin et al, Schweiz Arch Tierheilkd, Nov. 2000, 142/11:625-630.*
Imberechts et al, Adv. Exp. Med. Biol., 1997, 412:175-183.*
Dean-Nystrom et al, Vet. Microbiol., 1993, 37:101-114.*
Bijlsma et al, Infection and Immunity, Sep. 1982, 37/3:891-894.*
Walker, Vaccine, 2005, 23:3369-3385.*
Nagy et al, International J. Medical Microbiology, 2005, 295:443-454.*
Clarke et al, Diagnostic Microbiology and Infectious Disease, 2001, 41:93-98.*
Sanchez et al, Current Opinion in Immunology, 2005, 17:388-398.*
Girard et al, Vaccine, 2005, Article in Press, "A review of vaccine research and development: human enteric infections", 19 pages.*
Verdonck et al, Vaccine, 2002, 20:2995-3004.*
Snoeck et al, Veterinary Immunology and Immunopathology, 2003, 96:219-227.*
Verdonck et al, Veterinary Immunology and Immunopathology, 2005, 103:21-29.*
Barry et al, Vaccine, 2005, Article in Press, "Immunogenicity of multivalent Shigella-ETEC candidate vaccine strains in a guinea pig model", 8 pages.*
Saif, Veterinary Immunology and Immunopathology, 1996, 54:163-169.*
Olasz et al, FEMS Microbiology Letters, 2005, 244:281-289.*
Nagy et al, Microbial Pathogenesis, 1997, 22:1-11.*
Attridge et al, Vaccine, 1988, 6/5:387-389.*
Walker, Vaccine, 1994, 12/5:387-400.*
Fuentes et al., "Inoculation of Non Pathogenic *Escherichia coli* to Control Disease and Reduce Antibiotic Usage", Proceedings of the 18th IPVS Congress, Hamburg Germany, 2004.

(Continued)

*Primary Examiner*—Nita M. Minnifield
(74) *Attorney, Agent, or Firm*—Abelman, Frayne & Schwab

(57) ABSTRACT

The invention relates to a strain suitable for producing a live, orally applicable *Escherichia coli* vaccine for the prevention of post-weaning diarrhoea in pigs, and the procedure suitable for producing that strain. The essence of the strain is that the enterotoxin-free and originally wild-type *Escherichia coli* strain simultaneously produces two adhesive fimbriae (F4 and F18), whereas the essence of the procedure is that the enterotoxin-producing ability if the wild, pathogenic, enterotoxigenic *Escherichia coli* strain originally capable of producing enterotoxins and F18 fimbriae is abolished by a genetic intervention while retaining the ability of the strain to produce F18 fimbria facilitating adhesion to the small intestinal wall of weaned piglets, and subsequently the strain thus modified is rendered capable of producing a further surface adhesion fimbria (F4).

4 Claims, No Drawings

OTHER PUBLICATIONS

Osek, "Oral Immunization of Piglets with *Escherichia coli* Vaccine I. Serum Antibodies", Bull. Vet Inst. Pulawy, 33-41, (1999).

Osek, "Oral Immunization of Piglets with *Escherichia coli* Vaccine, II Intestinal Antibodies", Bull. Vet Inst. Pulawy, 43-52 (1999).

* cited by examiner

ESCHERICHIA COLI STRAIN FOR AN ORAL VACCINE AGAINST POST-WEANING DIARRHEA IN PIGS

CROSS-REFERENCE TO RELATED APPLICATIONS

This application is a §371 of PCT/HU00/00026 filed on Mar. 29, 2000 and claims the priority benefit of Hungarian Application Ser. No. P 99 00 836 filed on Mar. 31, 1999.

BACKGROUND OF THE INVENTION

1. Field of the Invention

The subject-manner of the invention is a strain for production of a live, orally applicable *Escherichia coli* vaccine for the prevention of post-weaning diarrhoea in pigs, and the procedure suitable for producing that strain.

2. Description of Related Art

Diarrhoea caused by so-called enterotoxigenic *Escherichia coli* (ETEC) bacteria is one of the most severe, commonly occurring diseases of pig rearing, which usually causes 5–15% mortality in newborn (baby) piglets, and subsequently gives rise to losses of similar magnitude after weaning. Losses arising from the costs of medication, growth retardation and other consequences of the disease are much more substantial than direct damage due to mortality. The pathogenesis of the disease is essentially as follows: after getting into the intestinal tract of pigs, ETEC bacteria adhere to the wall of the small intestine with the help of their surface protein antigens (fimbriae), multiply there in large numbers, and transfer their heat-stable or heat-labile toxins (STa, STb, LT enterotoxins) directly to the intestinal epithelial cells. Due to the effect exerted by the toxins, the fluid-absorbing activity of intestinal epithelial cells will cease and the cells will secrete a large volume of fluid into the intestinal lumen. As a result, clinically severe diarrhoea will develop. Thus, the first step in the pathogenesis of the disease entity is the adherence of pathogenic ETEC bacteria to the intestinal wall (which adherence itself does not cause disease), followed by the effect exerted by the toxins on the intestinal epithelial cells (this results in diarrhoea). [Fairbrother, J M.: *Enteric colibacillosis*. In: Leman A D, Straw B E, Mengeling W L, D'Allaire S, Taylor D, eds. *Diseases of Swine*, 7th edn, Ames, Iowa state University Press, 1992: 489–497.]

In the past 10–15 years, several vaccines have been developed and marketed for the control of neonatal coli diarrhea. Through vaccination of the dams (sows) (so-called parenteral vaccination) these vaccines induce the production of specific antibodies to pathogenic ETEC strains in the sow's milk. These antibodies will provide newborn and baby piglets with adequate protection. The antibodies present in the mother's milk specifically inhibit the growth of pathogens located in the intestinal lumen and on the intestinal wall. [Moon H W.: Protection against enteric colibacillosis in pigs suckling orally vaccinated dams: Evidence for pili as protective antigens. *Am. J. Vet. Res.* 1981: 42, 173–177.]

For the control of post-weaning coli diarrhoea of piglets, no effective vaccine is known yet which could be used in a manner similar to that described above. This is mostly due to the fact that vaccines administered parenterally (i.e. not through the alimentary canal) predominantly facilitate the production of circulating antibodies which, however, can hardly, or not at all, reach the enterotoxic *Escherichia coli* bacteria located in the intestinal lumen and on the intestinal wall. Therefore, certain researchers attempt to administer the antibodies itself (e.g. specific antibodies produced in the yolk of chicken eggs) into the gastrointestinal tract of piglets by the oral route (e.g mixed in the feed) [Zuniga A, Yokohama H, Albicker-Rippinger P, Eggenberger E, Bertschinger H U.: Reduced intestinal colonization with F18-positive enterotoxigenic *Escherichia coli* in weaned pigs fed chicken egg antibody against the fimbriae. *FEMS Immunol. Medical Microbiol.* 1997: 18, 153–161]. A further possible method of control is the use of orally applicable vaccines that exert their immunizing effect against ETEC bacteria in the digestive tract. Earlier vaccines of this type, suitable for immunizing the intestinal tract, contained inactivated microorganisms. In certain cases the continuous presence of such microorganisms in substantial amounts (in the feed) reduced the losses caused by post-weaning diarrhoea; however, nowadays such vaccines are used rarely or not at all due to their low reliability. In this case one of the main causes of failure is that heat treatment destroys those heat-labile, proteinaceous products of ETEC bacteria which are important for their virulence. These are the heat-labile enterotoxin, and the F4 [Orskov I, Orskov F.: Serology of *Escherichia coli* fimbriae. *Prog. Allergy* 1983: 33, 80–105.] and F18 [Rippinger P, Bertschinger H U, Imberechts H, Nagy B, Sorg I, Stamm M, Wild P, Wittig W.: Designations F18ab, and F18ac for the related fimbrial types F107, 2134P and 8813 of *Escherichia coli* isolated from porcine postweaning diarrhoea and from oedema disease. *Vet. Microbiol.* 1995: 45, 281–295.] fimbriae. Thus, they cannot exert their immunizing effect. As a consequence, such vaccines—to be produced primarily for immunizing the intestinal tract—must contain live microorganisms that can colonize the intestinal tract, can produce there the antigens important for protection continuously and in sufficient quantity, and can facilitate the immunity of the intestinal tract against them.

Live microorganisms capable of providing local protection (i.e. protection asserting itself on the mucous membrane) against pathogens can be developed either by inserting genes into innocuous laboratory strains or by altering certain properties of the pathogens. We chose the latter approach.

BRIEF SUMMARY OF THE INVENTION

The subject-matter of the invention is a strain suitable for producing a live, orally applicable *Escherichia coli* vaccine for the prevention of post-weaning diarrhoea in pigs, and the procedure suitable for producing that strain. The essence of the strain according to the invention is that the enterotoxin-free and originally wild-type *Escherichia coli* strain simultaneously produces two adhesive fimbriae (F4 and F18), whereas the essence of the procedure according to the invention is that the enterotoxin-producing ability of the wild, pathogenic, enterotoxigenic *Escherichia coli* strain originally capable of producing enterotoxins and F18 fimbriae is abolished by a genetic intervention while retaining the ability of the strain to produce F18 fimbria facilitating adhesion to the small intestinal wall of weaned piglets, and subsequently the strain thus modified is rendered capable of producing a further surface adhesion fimbria (F4).

DETAILED DESCRIPTION OF THE INVENTION

The procedure is demonstrated on the example of a characteristic representative of ETEC strains capable of producing post-weaning diarrhea (the strain designated EC2173.

The strain EC2173 (O147:F18ac, STa, STb) is an *Escherichia coli* strain isolated from a severe case of post-weaning diarrhoea of pigs in Hungary and characterized by us [Nagy B, Casey T A, Moon H W.: Phenotype and genotype of *Escherichia coli* isolated from pigs with postweaning diarrhea in Hungary, *J. Clin. Microbiol* 1990: 26, 651–653. and Nagy B, Whipp, S C, Imberechts H, Bertschinger H U, Dean-Nytsrom E A, Casey T A, Salajka E.: Biological relationship between F18ab and F18ac fimbriae of enterotoxigenic and verotoxigenic *Escherichia coli* from weaned pigs with oedema disease or diarrhoea. *Microbial Pathogenesis* 1997: 22, 1–11.], which is unsuitable for taking up foreign plasmids under natural (or natural-like) conditions. Using the principle of plasmid incompatibility, the genetic element (plasmid) of that strain responsible for enterotoxin (STa, STb) production was removed. All this was done in such a way that the toxin-negative *Escherichia coli* strain EC2173 (NBI/36) could retain the ability to produce its original fimbriae (F18ac) facilitating its intestinal colonization.

It was already known that the STb enterotoxin gene of the entero-toxigenic *Escherichia coli* strain EC2173 was carried by a plasmid in the strain. In addition, a plasmid construct containing the STb toxin gene in "damaged" form (cut into two almost equal parts) and carrying a kanamycin marker gene (pTKm5-pMB1 replication origin $Amp^R$, $Km^R$) inserted into the toxin gene was introduced into the wild strain designated EC2173 by electroporation [Sambrook, Fritsch, Maniatis: *Molecular cloning—A Laboratory Manual* 1989, 1.75.], in order to achieve that the "damaged" STb toxin gene replaces the intact toxin gene of the virulence plasmid by double homologous recombination [Freifelder: *Microbial Genetics* 1987, 346–347.]. Control tests carried out after the experiments showed that the STb toxin gene was maintained in functional form in the strain despite insertion of the pTKm5. During further experiments utilizing the principle of plasmid in-compatibility, first the endemic virulence plasmid and the pTKm5 plasmid construct were successfully eliminated from the transformed EC2173 derivatives as described below.

The incompatible expulsive plasmid (pFOL547-pMB1 replication origin $Cm^3$, conjugative plasmid) was introduced into the pTKm5 carrying transformants by conjugation [Kondorosi å., Kiss Gy., Forrai T., Vincze, É., Bánfalvi Zs.: Circular linkage map of *Rhizobium meliloti* chromosome. *Nature* 1977 268 525–527.], then some selected (transconjugant) colonies were passaged (growth for 10–12 hours in GTS (minimal) nutrient medium containing 20 μg/ml chloramphenicol) in order to obtain Km and Tc sensitive (i.e. pTKm5 and pTc free) colonies (clones). After the $10^{th}$ passage, the antibiotic resistance pattern was determined (by replica plating after surface streaking onto GTS (minimal) agar containing 20 μg/ml chloramphenicol).

This was followed by another passage in order to accelerate expulsion of the pFOL547 plasmid. In the case of certain isolates it was observed that tetracycline resistance typical of the EC2173 wild strain was abolished together with chloramphenicol resistance. The results obtained by HindIII restriction enzyme analysis [Sambrook, Fritsch, Maniatis: *Molecular cloning—A Laboratory Manual* 1989, 1.82–85.] of total plasmid DNA purified from these tetracycline- and chloramphenicol-sensitive isolates showed that the endemic virulence plasmid and the pFOL547 plasmid had been lost (the strains had become sensitive to both Tc and Cm).

The isolates produced with the loss of the virulence plasmid had become sensitive to tetracycline; thus, the plasmid was designated pTc after the tetracycline resistance gene it carried. Based upon the PCR performed with a primer specific for the STa toxin gene [Alexa P., Rychlik I., Nejezchleb A., Hamrik J.: Identification of enterotoxin-producing strains of *Escherichia coli* by PCR and biological methods. *Vet. Med.* (Praha) 1997 Apr; 42(4): 97–100.] and the STb toxin gene specific Southern hybridization ]Lee C. H., Moseley S. L., Moon H. W., Whipp S. C., Gyles C. L., So M.: Characterization of the gene encoding heat-stable toxin II and preliminary molecular epidemiological studies of enterotoxigenic *Escherichia coli* heat-stable toxin II producers. *Infect. Immun.* 1983 42(1): 264–268.] tests the isolates proved to be defective for the STa and STb enterotoxin genes, while they continued to produce the F18ac fimbria (as demonstrated by agglutination and immunofluorescence tests [Nagy B, Whipp, S C, Imberechts H, Bertschinger H U, Dean-Nytsrom E A, Casey T A, Salajka E.: Biological relationship between F18ab and F18ac fimbriae of enterotoxigenic and verotoxigenic *Escherichia coli* from weaned pigs with oedema disease or diarrhoea. *Microbial Pathogenesis* 1997: 22, 1–11.]); thus, they had become suitable for further experiments aimed at the production of a vaccine strain.

In order to develop the vaccine strain, a gene cluster coding for the production of a further (the so-called F4) fimbria was also inserted into the toxin-negative (NBI/36) strain, as production of the F4 fimbria also enhances the ability of the strain to colonize the intestine of weaned pigs. The pDB88-102 plasmid suitable for the introduction of F4 fimbriae was produced from Mooi's FM205 strain [Mooi F R, Van Buuren M, Koopman G, Roosendaal E, DeGraf F K.: K88ab gene of *Escherichia coli* encodes a fimbria-like protein distinct from the K88ab fimbrial adhesin. *J. Bacteriol.* 1984: 159, 482–487.] by Bakker [Bakker D.: Studies on the K88 fimbriae of enteropathogenic *Escherichia coli*. *Akademisch Proefschrift*, Drukkerij Elinkwijk BV, Utrecht 1991.], who made it freely available to us for this purpose. The pDB88-102 plasmid contains the entire gene system (operon) regulating the production of K88ac fimbriae. The pDB88-102 plasmid was introduced into the atoxic NBI/36 strain by electroporation; the same operation can also be performed by conjugation or transformation [Freifelder: *Microbial Genetics* 1987, 253–268. and Sambrook, Fritsch, Maniatis: *Molecular cloning—A Laboratory Manual* 1989, 1.82–85.].

Electroporation (electro-transformation) of the strains specified above was done with a Bio-Rad Gene Pulser electroporation instrument, using a cuvette of D=2 mm and electroporation parameters of 25 μF, 400Ω and 2.5 kV. During transformation, approx. 1 μg pDB88-102 plasmid DNA was added to 100 μl electrocompetent bacterial cell [Maloy, Stewart, Taylor: *Genetic analysis of pathogenic bacteria A Laboratory Manual* 1996, 490–492.]. After electroporation, the bacteria were grown in 1.5 ml antibiotic-free LB broth at 37° C. for 1 hour, then after centrifugation (7500 rpm, 3 min) all bacteria were surface-streaked onto sheep blood agar containing 150 μg/ml ampicillin, and incubated at 37° C. for 18 hours. Subsequently the ampicillin-resistant colonies were grown to high numbers in LB broth containing 150 μg/ml ampicillin. The pDB88-102 plasmid was inserted into the atoxic derivatives of strain EC2173 (e.g. NBI/36) according to the procedure described above.

The thus modified *Escherichia coli* strains (designated NBI/36-9) can be characterised by the following phenotype: O147:K+, NM, F4ac, F18ac, Hly.

Post-weaning diarrhoea of pigs caused by *Escherichia coli* can be effectively prevented by the oral administration of the live culture of such a strain (e.g. $10^{18}$ *Escherichia coli*/dose) before and after weaning.

The invention claimed is:

1. A process for producing a nontoxic, fimbria producing *Escherichia coli* strain, which comprises the steps of:
   a) abolishing by genetic intervention the enterotoxin-producing ability of a wild pathogenic, enterotoxigenic *Escherichia coli* strain (Ec2173, O147:K+, NM, STa, STb, F18ac, Hly) originally adapted to producing enterotoxins and F18ac fimbria while retaining the ability of the strain to produce an F18ac fimbria;
   b) introducing an F4 plasmid into the strain by electroporation, conjugation, or transformation to produce a further surface adhesion fimbria (F4ac); and
   c) culturing the *Escherichia coli* strain (NBI/36-9) containing the plasmids for production of both F4ac and F18ac fimbria.

2. The process according to claim 1, wherein the enterotoxin-producing (STa, STb) ability of the enterotoxigenic *Escherichia coli* strain designated Ec2173 is abolished by removal of its coding plasmid (pTc).

3. The process according to claim 2, wherein the coding plasmid regulating the production of enterotoxins is expulsed by the introduction of an incompatible plasmid (pFOL 457).

4. The process according to claim 1, wherein the plasmid encoding the surface adhesion fimbria (4ac) is incorporated into the non-enterotoxigenic derivative NBI/36 of the enterotoxigenic *Escherichia coli* strain Ec2173, resulting in *Escherichia coli* strain NBI/36-9.

* * * * *